United States Patent [19]

Kraemer et al.

[11] Patent Number: 5,394,873
[45] Date of Patent: Mar. 7, 1995

[54] MONITOR FOR SURVEYING THE VITAL PHYSIOLOGICAL PARAMETERS OF A PATIENT UNDERGOING NMR IMAGING

[75] Inventors: Michel Kraemer, Durrenbach; Gérard Muller, Rohrbach-les-Bitche; Michel Lanoux, Altenstadt, all of France

[73] Assignee: Odam, S.A., Wissembourg, France

[21] Appl. No.: 181,863

[22] Filed: Jan. 13, 1994

Related U.S. Application Data

[63] Continuation of Ser. No. 797,331, Nov. 25, 1991, abandoned.

[30] Foreign Application Priority Data

Nov. 23, 1990 [FR] France .................... 90 14846

[51] Int. Cl.⁶ .................. A61B 5/024; A61B 5/055
[52] U.S. Cl. .................. 128/653.2; 128/653.5; 128/710; 364/413.03; 364/413.13; 364/708.1
[58] Field of Search ............. 128/653.1, 653.2, 653.5, 128/709, 710, 639, 640; 324/309, 318; 364/413.02, 413.03, 413.13, 708

[56] References Cited

U.S. PATENT DOCUMENTS

| | | | |
|---|---|---|---|
| 4,365,475 | 10/1982 | Neumann et al. | 128/709 |
| 4,685,467 | 8/1987 | Cartmell et al. | 128/640 |
| 4,715,385 | 12/1987 | Cudahy et al. | 128/709 |
| 4,727,882 | 3/1988 | Schneider et al. | 128/653.2 |
| 4,742,828 | 5/1988 | Sundström | 128/640 |
| 4,776,341 | 10/1988 | Bachus et al. | 128/653.3 |
| 4,951,672 | 8/1990 | Buchwald et al. | 128/653.5 |
| 4,972,852 | 11/1990 | Koob et al. | 128/653.2 |
| 4,991,580 | 2/1991 | Moore | 128/653.5 |
| 5,038,785 | 8/1991 | Blakeley et al. | 128/653.2 |
| 5,074,309 | 12/1991 | Gerdt | 128/653.2 |
| 5,138,260 | 8/1992 | Molyneaux et al. | 324/309 |

FOREIGN PATENT DOCUMENTS

| | | | |
|---|---|---|---|
| 0132785 | 2/1985 | European Pat. Off. . | |
| 0173130 | 3/1986 | European Pat. Off. . | |
| 0313173 | 4/1989 | European Pat. Off. | 128/639 |
| 0049539 | 2/1989 | Japan | 128/639 |
| 9005494 | 5/1990 | WIPO | 128/653.2 |

OTHER PUBLICATIONS

"Monitoring of Acutely Ill Patients during Nuclear Magnetic Resonance Imaging: Use of a Time–Varying Filter Electrocardiographic Gating Device to Reduce Gradient Artifacts", *Magnetic Resonance in Medicine*, vol. 6, No. 2, Feb. 1988, By R. Rokey et al., pp. 240–245.

*Primary Examiner*—Krista M. Pfaffle
*Attorney, Agent, or Firm*—Young & Thompson

[57] ABSTRACT

A general surveillance monitor to monitor the vital physiological signs of patients undergoing examination by nuclear magnetic resonance imaging is constructed such that each functional module of the monitor is individually protected from the electromagnetic environment and high frequency parasitic currents and such that the control assembly is a computer system without any magnetic storage.

4 Claims, 8 Drawing Sheets

MONITOR FOR SURVEYING THE VITAL PHYSIOLOGICAL PARAMETERS OF A PATIENT UNDERGOING NMR IMAGING

This application is a continuation of application Ser. No. 07/797,331, filed Nov. 25, 1991, now abandoned.

FIELD OF THE INVENTION

The present invention relates to a monitor for surveying the vital physiological parameters of a patient in the course of examination by the imaging technique of nuclear magnetic resonance.

BACKGROUND OF THE INVENTION

It is already known to provide self-contained apparatus for surveying a physiological parameter or a group of parameters of a patient in the course of medical examination.

The examination using the principle known as nuclear magnetic resonance of the magnetic spins of hydrogen protons present in the tissues, requires the creation of an electromagnetic medium or environment in which is inserted the object or the subject to be examined.

Herein, and in the following text, the electromagnetic medium or environment is understood to mean the entire space in which the three necessary fields conjugate their effects in known manner to give the image of the explored region of the subject in the course of examination, namely:

- the principal field which is a constant and homogeneous magnetic field of high intensity;
- the gradient, which is a magnetic field that varies as a function of space;
- the high frequency oscillating magnetic field in the radio frequency range.

During examination, the patient is stretched out on a couch and introduced into the tunnel-shaped space a tunnel called an examination tunnel constituting the central region of a high powered magnet usually immersed in a cryogenic medium to render it superconductive. In this tunnel exists and is concentrated the electromagnetic environment needed for the examination.

So as not to disturb this electromagnetic environment, the magnet, its housing and all the nearby associated apparatus are disposed in an electrically shielded chamber, whose walls or partitions are of sheet copper assembled without electrical discontinuity, forming a Faraday cage. Then, the examination and control signals are filtered by several batteries of specific filters and analyzed by circuits disposed outside the chamber and then made visible in the form of an image by one or several screens on a console.

The disturbances engendered by a surveillance apparatus affecting the good operation of the NMR examining equipment can be classified in two distinct categories:

- high frequency electromagnetic parasitic currents upsetting the action of the oscillating magnetic field. For this reason alone, all apparatus generating electromagnetic parasitic currents is prohibited in the shielded enclosure.
- deviations of the lines of force of the principal field outside the examination tunnel. These deviations arise from the presence of one or several ferromagnetic masses and are of such a nature as to modify the necessary uniformity of the principal field prevailing within the magnet. Care should accordingly be taken that the sum of the ferromagnetic masses present in the surveillance apparatus does not exceed a limit value which is a function of the distance which separates it from the superconductive magnet.

Conversely, the surveillance apparatus disposed adjacent the examination tunnel is subjected to disturbances due to the specific magnetic environment of the NMR imaging installation.

Thus, all apparatus whose operation is susceptible to being disturbed by the magnetic environment should not be used and requires important modifications and the adoption of protection. Of course, the use of any magnetic information supports or cathode ray tubes will be impossible.

Thus, no conventional complete information system can be useful, by reason of its mass memories and supports or various magnetic components.

Various adopted protections also cannot be dispensed with, because the central unit generates parasitic signals in the electric circuit.

Correspondingly, the control electronics of the display require high operating frequencies generating parasitic currents adapted to disturb the operation of the NMR imaging installation.

Thus, the proper operation of a surveillance apparatus adjacent an NMR imaging installation gives rise to numerous difficulties not yet solved at present.

A patient, such as an accident victim or premature baby placed in the examination tunnel, requires continuous surveillance by a doctor or qualified person, and the possibility of rapid intervention in the case of a physiological incident.

Furthermore, the straightness of the examination tunnel and its length adapted to accommodate the entire body, do not provide surveillance personnel with a sufficient field of vision to conveniently observe the patient in the course of examination.

Still further, the very high magnetic field in this region does not permit the use of any conventional assembly, for example surveillance optics using one or several video cameras.

It must of course be added, that this type of surveillance would not be sufficient to give information as to the condition of the patient and the immediate care needed by him in the case of momentary faintness.

Because of the impossibility of achieving even this minimum visual surveillance, the need for continuous automatic general surveillance assumes even greater importance.

Furthermore, a surveillance apparatus external to the insulating chamber, even if it were technically possible and operational, would not be of interest because of the pressing need for the surveillance personnel to be located beside the patient to intervene immediately in the case of fainting by the latter.

The surveillance doctor cannot enter into the shielded chamber in the course of examination under pain of rendering false the measurements, and it is out of the question, from a standpoint of cost, to devote two persons to this task.

Thus, this impossibility of suitably ensuring surveillance by an apparatus adjacent the NMR imaging examination equipment, not only does not square with the use of modern examination techniques, but constitutes a hardly permissible neglect in the case of patients who are frail or in a serious condition.

Also, the presence of a surveillance apparatus within the interior of the shielded chamber itself crowds the latter.

This important need, not yet satisfied at present, has been the subject of repeated efforts that are sustained and of great magnitude on the part of inventors to conceive and perfect automated surveillance functioning in a satisfactory manner adjacent the examination tunnel.

The present invention has for its object to operate a surveillance monitor in the shielded chamber and adjacent the superconductive magnet for medical imaging by nuclear magnetic resonance and thus to permit surveillance personnel to stay close to the patient and continuously have information on his condition.

Thus the surveillance apparatus according to the invention permits a person charged with surveillance and positioned beside the patient, simultaneously to know his condition and to be able to intervene immediately in case of faintness or difficulties.

The detailed technical characteristics and various other advantages are contained in the description which follows, given by way of non-limiting example with reference to the accompanying drawings, in which:

SUMMARY OF THE INVENTION

The general inventive idea consists in conceiving and constructing a surveillance monitor of a completely new type, for several vital physiological parameters detected in a patient, which monitor will be capable of providing precise and reliable measurements under the conditions of an intense magnetic environment existing immediately adjacent a Nuclear Magnetic Resonance imaging installation, hereinafter NMR imaging, and conversely not to disturb by its operation the signals detected and analyzed by this NMR imaging installation.

DETAILED DESCRIPTION OF THE INVENTION

Figure 1:
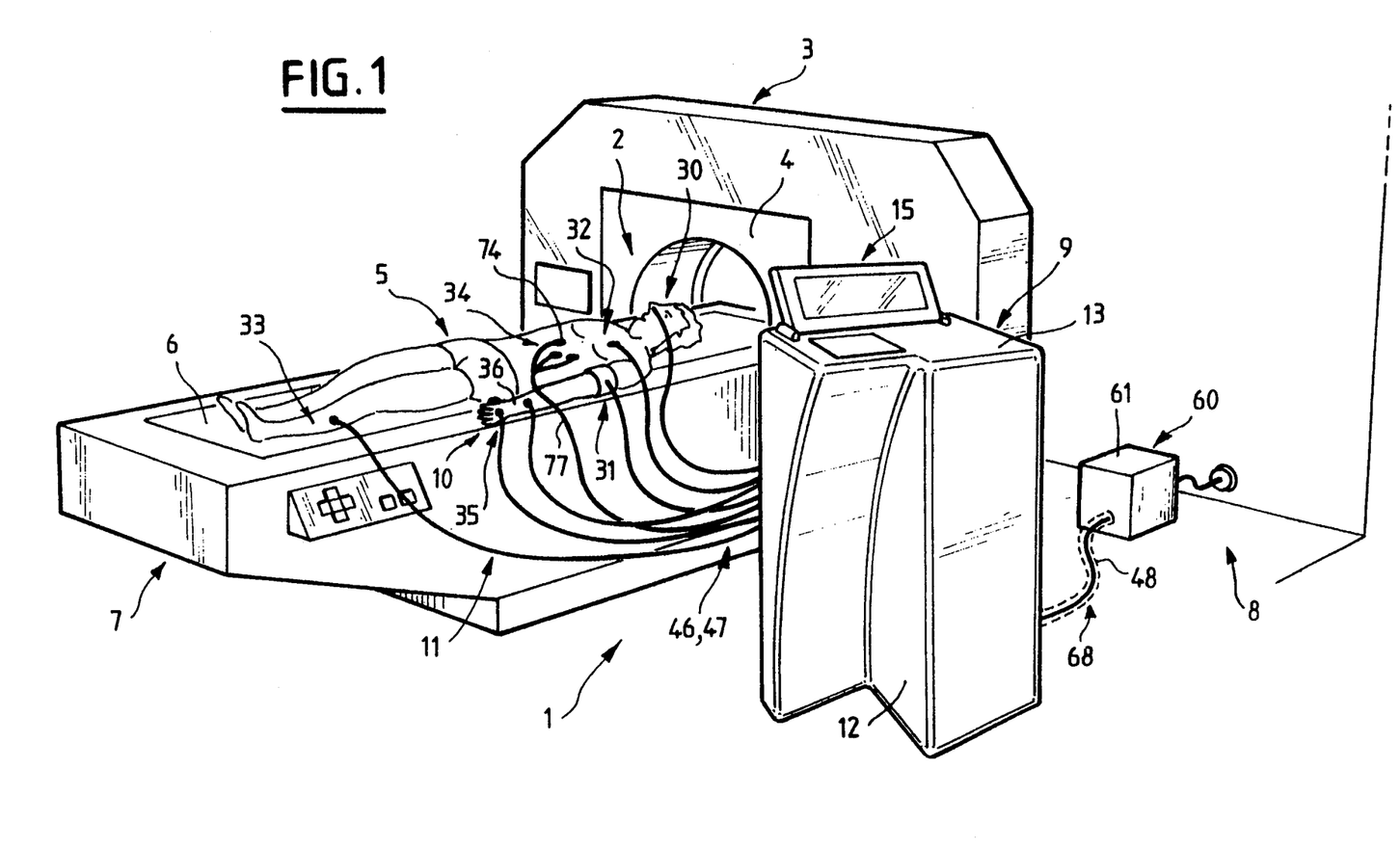
FIG. 1 is an overall perspective simplified view of the nuclear magnetic imaging examination equipment and of the monitor according to the invention disposed adjacent it.

There is shown in FIG. 1 the embodiment of an assembly of an NMR imaging installation 1 comprising an NMR imager which is comprised essentially on the one hand of an examination tunnel 2 in a casing 3 sheltering a high powered electromagnet 4 so as to examine a patient 5 disposed in known manner on a couch 6 provided on a support 7, in an electrically shielded chamber 8 which is sealed to electromagnetic radiation, and on the other hand a control desk external to the shielded chamber (not shown). There is disposed immediately adjacent the tunnel of the imager a surveillance monitor 9 according to the invention which detects, analyzes and surveys a plurality of vital physiological parameters of a patient 5 disposed in the examination tunnel 2 by means of an assembly of electrodes or detectors such as 10, adapted to the types of parameters surveyed, connected to the monitor 9 by a multifilament and multiconduit connector 11.

Figure 2:
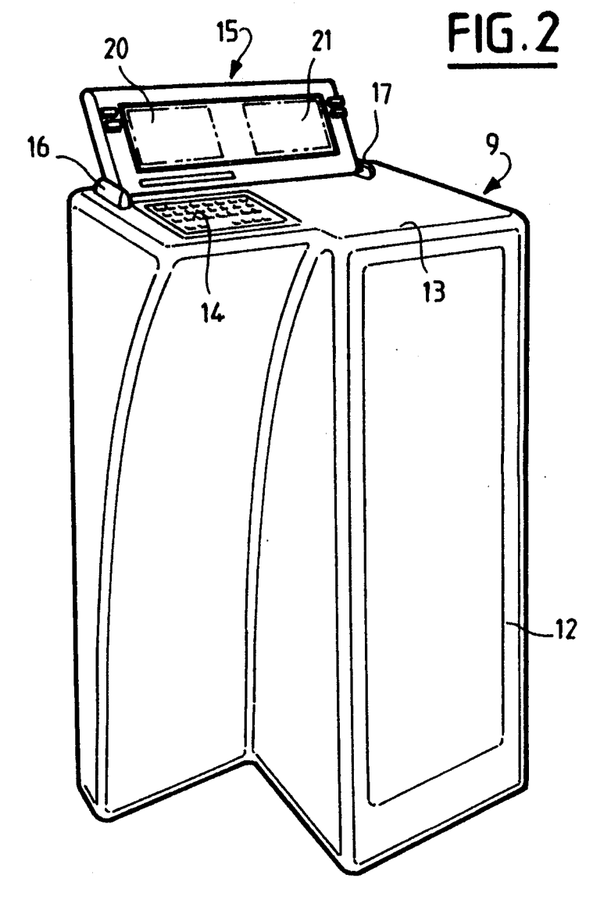
FIG. 2 is a perspective assembly view of the monitor according to the invention, seen from the front.
Figure 3:
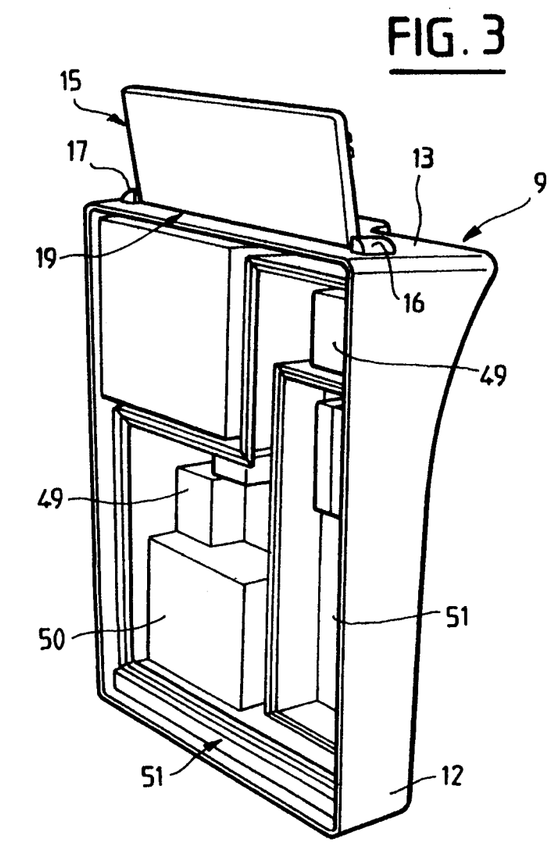
FIG. 3 is a perspective assembly view of the monitor according to the invention, seen from the rear.

There will first be described the monitor 9 in its entirety, that is to say as to its overall characteristics, with reference to FIGS. 1 to 3.

The monitor 9 is an apparatus resting upright on the floor, provided with a rearwardly opening housing 12, providing at its top a worktable 13 comprising a control keyboard 14 to communicate with the operator and a display panel 15 pivotally mounted on two pivots 16 and 17 on opposite sides of the panel, between a retracted position on the table, which is a transport position, and an ergonometric work position whose inclination is appropriate to facilitate reading. Program contacts preprogrammed in known fashion to be correlated with the messages appearing on the screen are, for example, disposed at the bottom of the display panel.

Within the housing and below the worktable 13 is located a central control and display unit 18 which directs the various operational modules and controls the display of the surveyed parameters in alphanumeric and graphic form on the display panel 15. This central unit is also called a control-display unit because of its principal function. It is also referred to as CPU.

Figure 4:
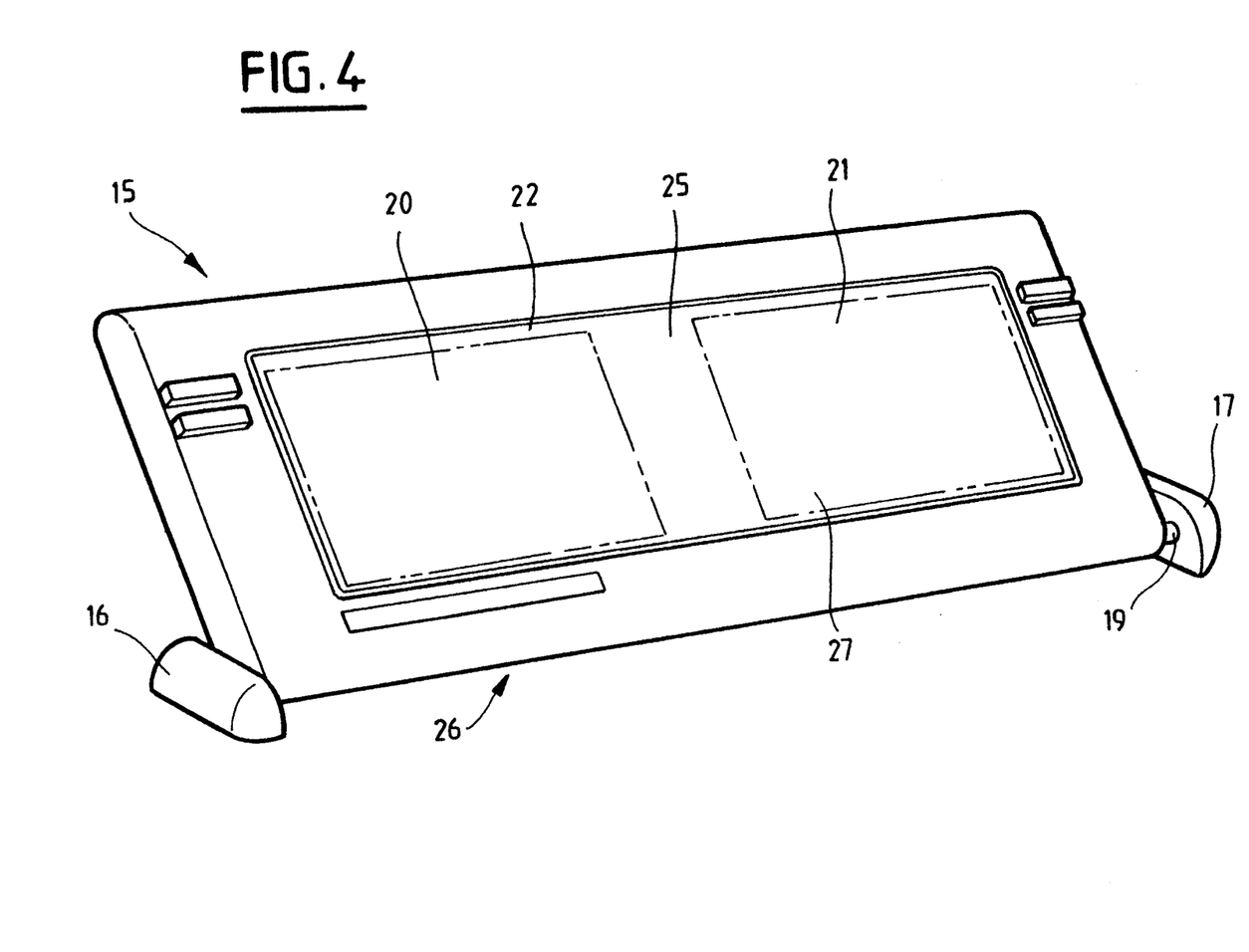
FIG. 4 is a perspective view of the display panel.
Figure 5:
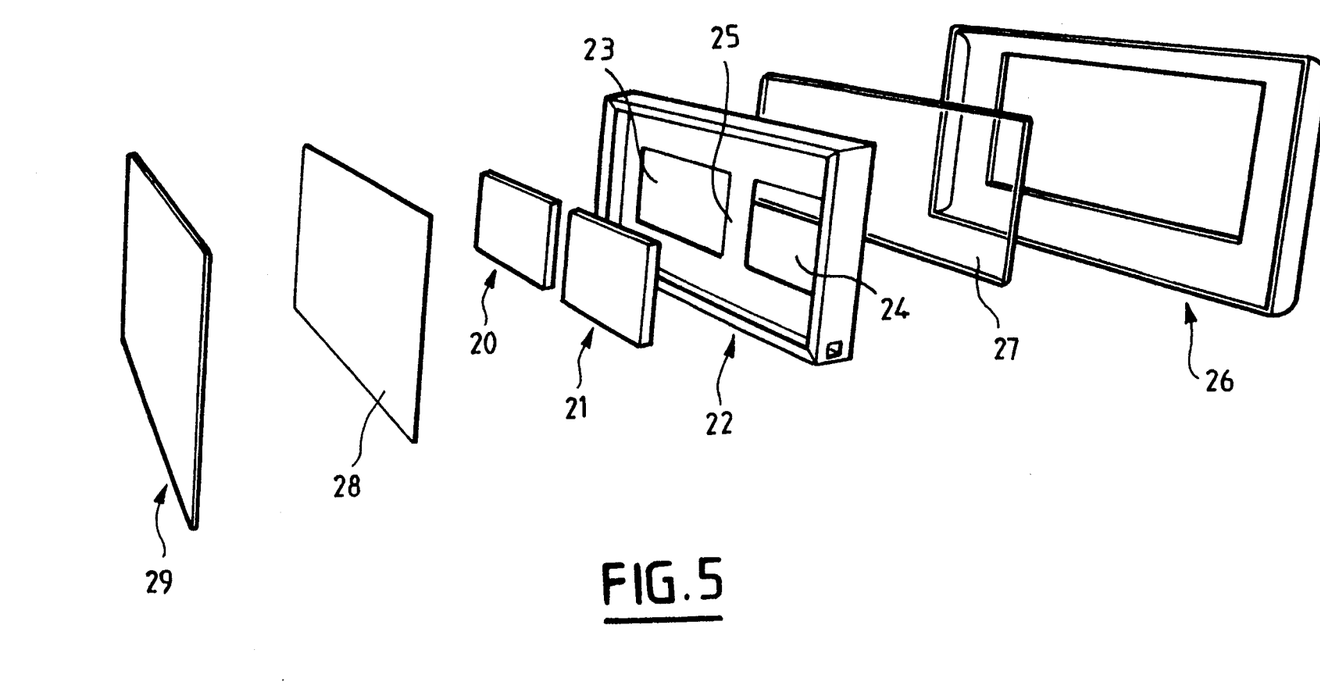
FIG. 5 is an exploded perspective view of the display panel.

As shown in FIGS. 4 and 5, the display panel 15 is mounted pivotally about a horizontal axis 19 on the upper surface of the apparatus.

It is comprised by two flat separate screens 20 and 21 using an electroluminescent cell matrix.

These flat screens 20 and 21 are mounted juxtaposed in a flat frame 22 in a panel forming a shielding chassis in which they are appropriately secured.

This frame comprises on its forward face two upwardly facing juxtaposed openings 23 and 24 corresponding to the position of the screens.

These openings are separated by a transverse covering strip 25.

The assembly is maintained in a frame envelope 26 of the panel type maintaining against the screens two shielded panes 27 and 28 providing front and rear facings.

These panes are transparent, but shielded, which is to say opaque to electrical and electromagnetic radiation.

This shielding is constituted by a sheet bearing on its internal face a transparent metallization, connected to the frame 22.

The assembly is closed on its rearward surface by an opaque plate 29.

These different members constituting the display panel are shown independently in FIG. 5 and in the assembled condition in FIG. 4.

Thus the screens are enclosed on all sides by suitable electrical and radio electrical protection from inside to outside and conversely, to provide the visualization and display panel such as 15.

Figure 6:
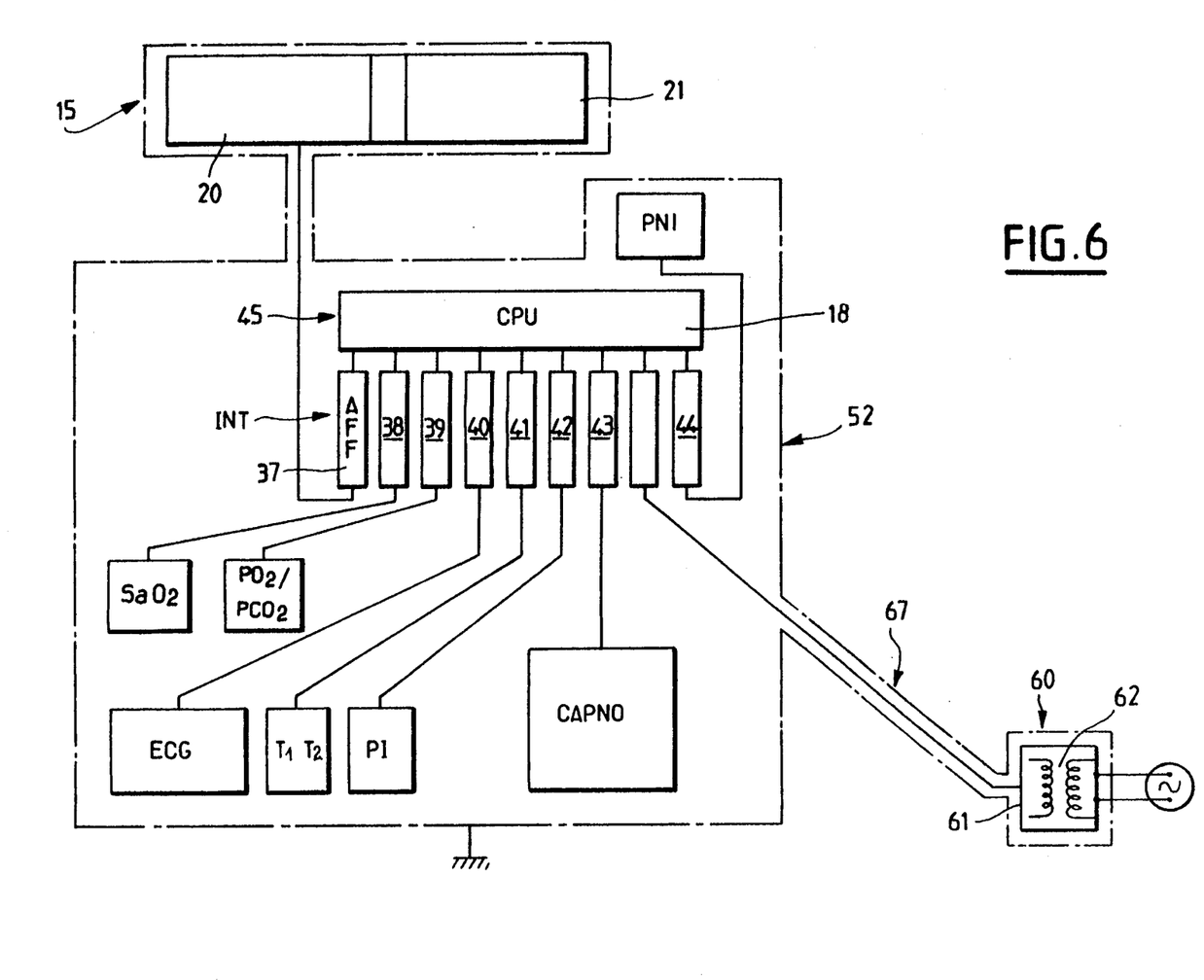
FIG. 6 is a schematic view of the various operational units.

By way of non-limiting example, the illustrated monitor comprises the following surveillance modules schematically shown in FIG. 6, to which more particular reference will now be had:

a module for surveillance of capnography-respiration which measures the gases exhaled by the patient with the aid of an appropriate buccal or nasal mouthpiece 30, and hereinafter designated and called CAPNO module;

a module for surveillance of the arterial pressure of the patient by a non-invasive technique, with the aid of an arm band 31 hereinafter referred to and called PNI module;

a module for surveillance of temperatures at different points on the patient, for example at two points, with the aid of two temperature probes 32 and 33 measuring two temperatures T1 and T2, hereinafter referred to and called T1T2 module;

a module for electrocardiographic surveillance hereinafter referred to and called EKG module, whose parameters are detected by electrodes such as 34 for receiving the electrocardiogram signal;

a module for surveillance of the oxygen saturation of the hemoglobin, for example by a transcutaneous process, hereinafter referred to and called $SaO_2$ module, combined with a detector 35 corresponding to the process used;

a module for the surveillance of partial pressures of oxygen and of carbon dioxide dissolved in the blood, hereinafter referred to and called PO2/PCO2 module, combined with a specific detector 36;

a module for the invasive surveillance of the arterial pressure PI by the aid of a detector in contact with the blood of the patient.

Each above module, performing a surveillance function known per se, is associated with other modules and operated by an assembly functional unit associated with a display card and a supply card.

Moreover, the monitor comprises a principal operating card 18 called a control-display card, combined with a display card 37 also designated AFF and with interface cards referenced 38 to 44 and also designated by INT appropriate to the functions of the various surveillance modules, the assembly being hereafter termed a control-display unit 45, whose essential function consists in controlling the assembly of the modules, the display of the parameters and the interfacing with the user and with the modules.

The monitor also comprises a certain number of internal conductors connecting each measurement module to the control-display unit 45, and the multifiber and multiconduit connector 11 bringing together a number of external conductors connecting each measurement module to its corresponding detector or detectors, referenced hereinafter by conductive connections such as 46 and tubular connections 47.

Figure 8:
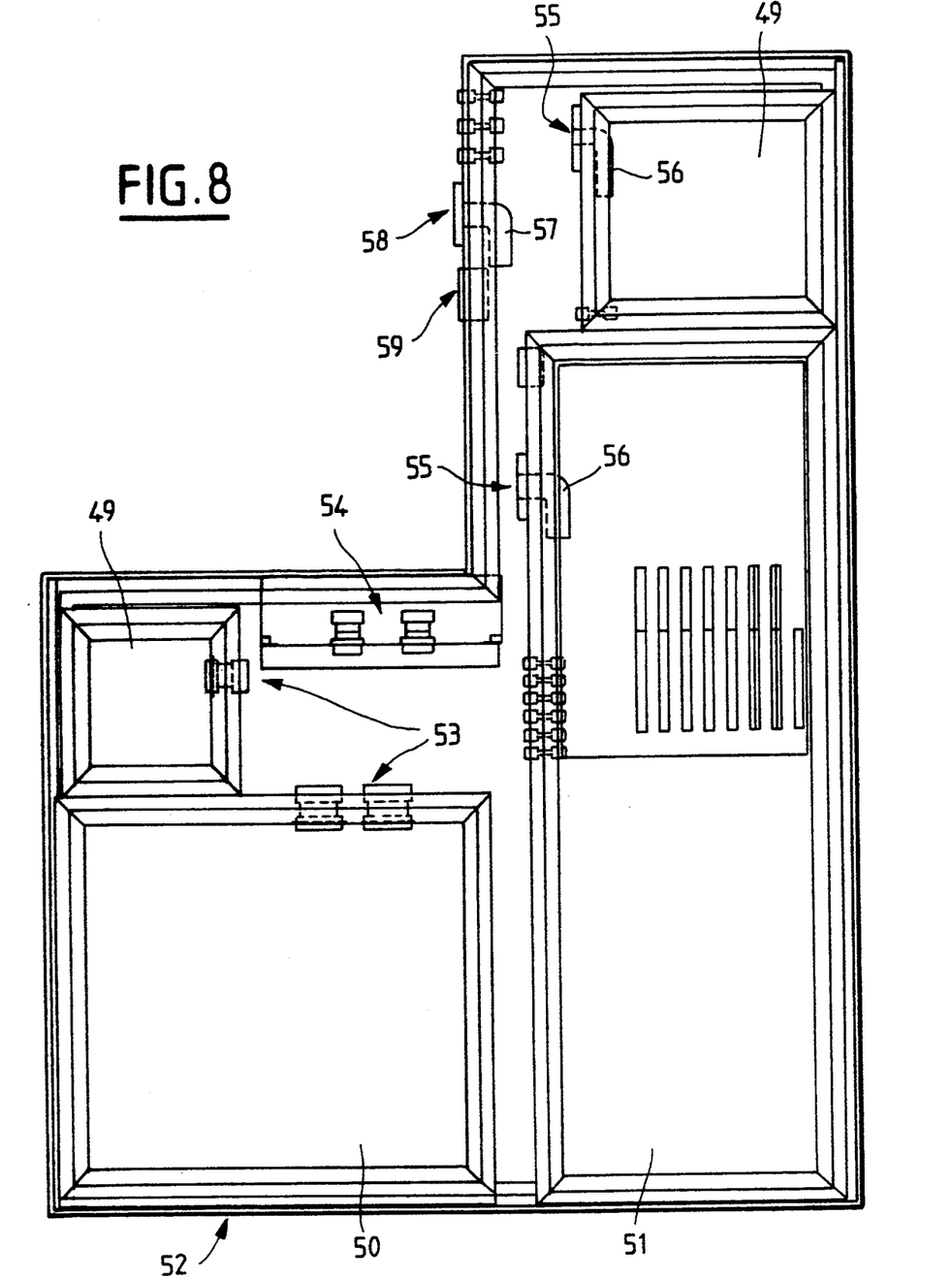
FIG. 8 is a general schematic view in elevation of the technical compartments illustrating the arrangement of the shielding chambers and their ventilating outlet.

So as to avoid electromagnetic emissions by the external conductors which may form antennas, and internal conductors for connection and supply, emissions which would disturb the magnetic and electromagnetic environment and the operation of the NMR imaging installation, the following constructional characteristics of the apparatus are adopted:

all the conductors are sheathed with shielding such as 48 whose ends are connected to the bodies of the apparatus and the shielded chamber;

the lengths of the conductors are optimized so as to reduce by the maximum the lengths which can radiate;

each module or group of modules is enclosed in a casing such as 49, 50 or 51, small, medium or large (FIGS. 3 and 8) of copper or of non-magnetic material impervious to electromagnetic radiation, whose object is to diminish the residual radiation about these casings; these casings are superposed, and fixed to each other;

the assembly of casings is disposed in a principal housing 52 of non-magnetic material and of sufficient mechanical strength and also sealed against electromagnetic radiation, for example of stainless steel, so as to avoid residual radiation to the exterior of the monitor and to improve the protection of the NMR imaging installation;

the assembly of outputs of the electric signal conductors through each casing or the principal housing is filtered with the aid of filtering connectors, respectively small and large, such as 53 and 54 (FIG. 8), disposed at each of the outputs;

the number of conductors is optimized so as to reduce the number of outputs, therefore the number of filtering connectors to be used and the risks of escape of radiation and its transmission;

each housing 49, 50 and 51 and the casing 52 have the general shape of a box with an upright rear door. The sealing of each closure relative to electromagnetic emissions is effected by any suitable means, for example by a shielding braid squeezed between the door and the casing or by leaf springs;

an output passage such as 55, in the form of metallic elbows such as 56 of piping, ensures the passage of the fluid connections and the communication with the exterior of each housing, while protecting the interior from direct radiation. Another elbow 57 constitutes the output 58 of the principal casing 52.

The first object of the presence of the housings relates to the residual radiation which must be as low as possible in the principal casing, to increase the effectiveness of filtering of the conductors leaving to the exterior.

A second object of the presence of the housings is that, if they were not there, each conductor leaving a given module could accumulate and emit the disturbances created by the module, but also transmit those emanating from the other modules, increasing the residual field in the principal casing 51 and rendering less effective the filtering of the outlet which is effected by the general outlet conductor 59 adjacent the outlet of the principal casing.

Simultaneously and fundamentally, the monitor is conceived so as not to be subject to disturbances of the NMR imaging installation, particularly those due to the very strong magnetic field existing in its immediately vicinity, but decreasing as a function of distance.

The principal intense magnetic field which is developed having a constant value, it is without effect on the operation of the electronic components such as the transistors, integrated circuits, but it prevents the use of mass memories with magnetic supports such as hard disks, diskettes, magnetic tapes . . . , which are replaced by solid memories in the card of the control-display unit.

Moreover, the behavior of each module in the electromagnetic environment has had to be individually studied.

Figure 7:
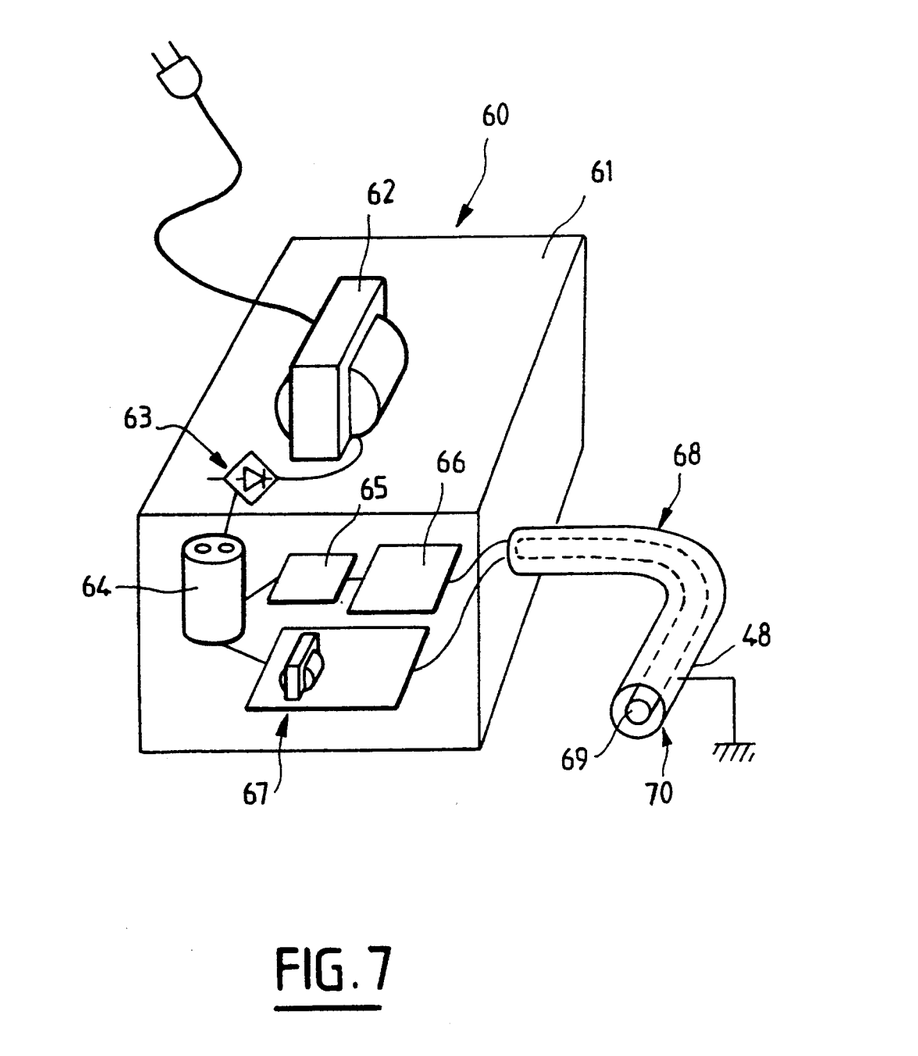
FIG. 7 is a schematic view of the supply of the monitor showing its emplacement relative to the body of the apparatus.

The monitor is electrically fed by a general supply 60. It is present in the form of a unit constituting a housing 61 enclosing the different circuits and components. It comprises a principal transformer 62, a rectifying circuit 63 and a filter 64, a regulation circuit 65 and a general control Stop/Go circuit 66 and a transformer 67 spaced from the CAPNO module. It is preferred to provide the general feed 60 outside the casing of the apparatus to which it is connected by a supply and control cable 68, and to space it as far as possible from this latter while remaining within the shielded chamber (FIG. 1).

The supply housing 61 is connected to the overall mass of the apparatus and of the shielded chamber, as well as the shielding of the connector cable 68.

This latter is constituted by a core 69 formed from a plurality of conductors, covered with a single or double shield 70 or several successive shielding envelopes.

If necessary, the assembly will be placed in a metallic profile, gutter or the like, connected to the overall body.

Another arrangement is also provided adjacent the general feed and the monitor-supply connector cable 68.

Because of the spacing, according to the invention, of the supply, the voltage drop in the connector cable is not negligible as to the voltage delivered. It may be necessary accordingly to increase the continuous supply voltage and to use a voltage supply adjustable specifically to the monitor, delivering a greater voltage than that of the standard supplies for microcomputers.

Figure 9:
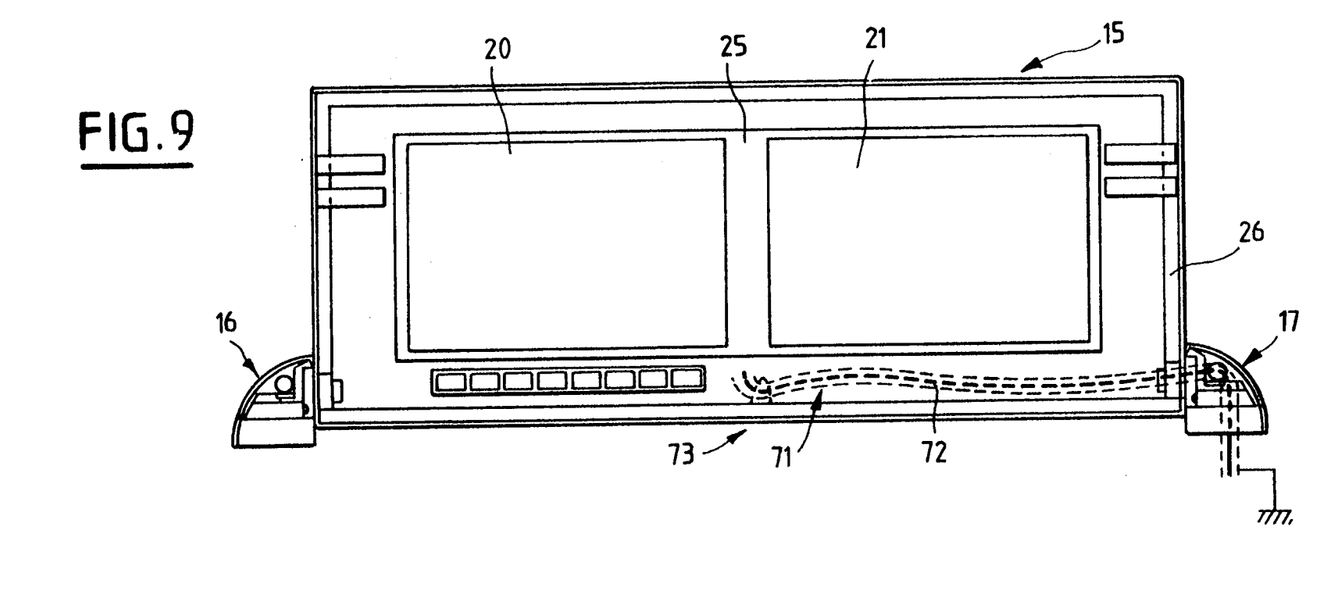
FIG. 9 is a simplified perspective view of the outlet for the cable connecting the body of the apparatus and the display panel.

Moreover, the output of the connecting conductors between the worktable 13 of the monitor and its pivoting display panel 15 should not be filtered, to keep the signals intact.

To have protection nevertheless, the specific solution adopted consists in not interrupting the continuity of the shielding between the screen and the principal casing 52 whereby the housings and the casing behave as a single Faraday cage.

To this end, the connecting conductors for the supply signals, sweep signals, the analysis signals and signals for the keyboard 14 are gathered in a cable 71 which passes through one of the axes of articulation 16 or 17 of the display panel 15, whose internal diameter is correspondingly chosen. Moreover, the conductors are covered with a flexible shielding sleeve such as 72 in electrical connection with the principal casing 52 of the monitor and with the frame 22 of the display panel 15.

To solve the problem of resistance to twisting of the connecting conductors along the axis of articulation, the fixed point 73 for connection of the conductor-screen is placed in the middle of the display panel, so as to leave a sufficient length of conductor free from torsion.

The arrangement of the detectors in the electromagnetic environment has also been studied.

Figure 10:
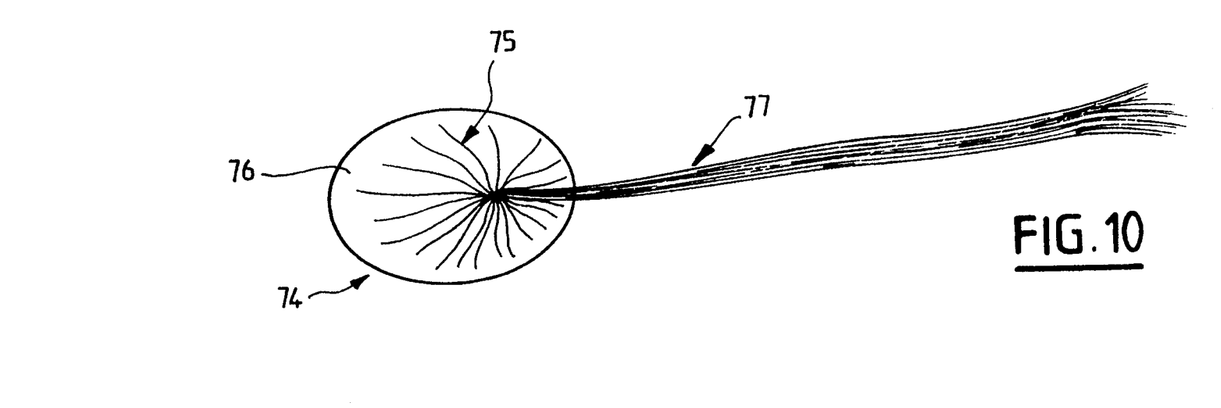
FIG. 10 is a schematic plan view of an electrocardiograph electrode.

Thus, the usual electrodes for electrocardiography have had to be replaced, because the metallic portions of the electrode can, in this electromagnetic environment, provoke burning of the skin, and the removable connection between the electrode and the connecting wire with the monitor gives rise to electromagnetic disturbances. These electrodes have been replaced by electrodes 74 formed of strands of wires 75 of amorphous carbon in a generally radial arrangement on a self-adhesive flat support 76, electrically connected to the corresponding module by a conductive connection 77 constituted by the prolongation of the strands of carbon forming the electrode (FIG. 10).

In the case in which the gradient induced in the parasitic currents in the monitor-detector connecting wires gives rise to disturbance of the transmitted electric signals, and therefore of the displayed curves and values, a first solution consists in changing the nature of the transmitted signal. This latter solution is particularly adaptable to the $SaO_2$ module for which it is desired to transport the luminous signal of the detector by optical fiber to the $SaO_2$ module of the monitor, then to transform the electrical signal to the interior of the housing using the appropriate transductors.

As to the electrical and fluidic connection between the modules PNI and CAPNO and their corresponding detectors, it should be noted that this is by tubes in which circulate air under pressure or gas specimens, which therefore do not conduct electrical signals. As a result, the outputs of these tubes, on the one hand adjacent the housings of modules and on the other hand adjacent the principal casing, do not require filtering connectors for electromagnetic parasitic currents. Said outputs are however provided with metallic elbows described above relative to the output plane for avoiding the straight line emission of residual electromagnetic radiations perpendicular to the output plane.

It is of course to be understood that apart from the described means, various obvious modifications and simple variations are included within the scope of the present invention.

We claim:

1. Monitor for surveying vital physiological parameters of a patient undergoing examination in a tunnel of a nuclear magnetic resonance imaging means for detecting and analyzing signals, wherein said monitor comprises:
   a shielded principal casing;
   means for detecting vital physiological parameters of the patient;
   an assembly of surveillance modules;
   shielded conductor means for connecting the detecting means to the surveillance modules;
   a plurality of shielded housing means for surrounding each of the surveillance modules, said shielded housing means being disposed in said shielded principal casing;
   a central means for controlling and displaying information relating to the vital physiological parameters detected by the detecting means, wherein said central means is a computer system free from magnetic storage;
   wherein the shielding of said principal casing and said plurality of housing means and said conductor means shield the surveillance modules such that they operate noninterferingly with said signals in a region adjacent to the nuclear magnetic resonance imaging means.

2. Monitor according to claim 1, wherein the central controlling and displaying means includes a control-display card with a solid-state memory storage and further wherein the surveillance modules each include a card-controlling means for acquiring the vital physiological parameters from the detecting means.

3. Monitor according to claim 1, further comprising:
a plurality of articulating pivot elements having a common pivot axis;
a display panel being pivotally mounted by the plurality of articulating pivot elements and having a frame;
conductor means, being passed through the common pivot axis of the articulating pivot elements, for supplying electricity to the principal casing and to the frame of the display panel; and
a flexible sleeve means for shielding the conductor means.

4. Monitor according to claim 1, further comprising:
gas tube means for providing gas to the patient.

* * * * *